(12) United States Patent
Kurz et al.

(10) Patent No.: US 9,237,279 B2
(45) Date of Patent: Jan. 12, 2016

(54) METHOD OF INVESTIGATING A SOLID SAMPLE

(71) Applicant: Bergen Teknologioverfoering AS, Bergen (NO)

(72) Inventors: Tobias Herbert Kurz, Bergen (NO); Simon John Buckley, Bergen (NO); John Anthony Howell, Bergen (NO)

(73) Assignee: Bergen Teknologioverfoering AS, Bergen (NO)

( * ) Notice: Subject to any disclaimer, the term of this patent is extended or adjusted under 35 U.S.C. 154(b) by 366 days.

(21) Appl. No.: 13/887,519

(22) Filed: May 6, 2013

(65) Prior Publication Data
US 2014/0327760 A1 Nov. 6, 2014

(51) Int. Cl.
| | |
|---|---|
| *G01N 21/25* | (2006.01) |
| *H04N 5/33* | (2006.01) |
| *G01N 21/31* | (2006.01) |
| *G01V 8/20* | (2006.01) |
| *G01V 99/00* | (2009.01) |
| *G01J 3/28* | (2006.01) |

(52) U.S. Cl.
CPC ............... *H04N 5/332* (2013.01); *G01N 21/31* (2013.01); *G01V 8/20* (2013.01); *G01V 99/00* (2013.01); *G01J 3/2823* (2013.01)

(58) Field of Classification Search
USPC ........ 356/328, 73, 51, 445; 348/135, 144, 42, 348/169, 222.1, 346; 250/339.05, 339.11, 250/372
See application file for complete search history.

(56) References Cited

U.S. PATENT DOCUMENTS

| | | | |
|---|---|---|---|
| 4,587,424 A | 5/1986 | Grau | |
| 6,587,575 B1* | 7/2003 | Windham et al. | 382/110 |
| 7,933,018 B2* | 4/2011 | Vannuffelen et al. | 356/432 |
| 2002/0159098 A1* | 10/2002 | Kleiman | 358/474 |
| 2004/0232339 A1* | 11/2004 | Lanoue | 250/339.05 |
| 2007/0265783 A1* | 11/2007 | Mound | 702/8 |
| 2008/0102487 A1* | 5/2008 | Yao et al. | 435/34 |
| 2008/0199080 A1* | 8/2008 | Subbiah et al. | 382/190 |
| 2009/0015686 A1* | 1/2009 | Alsberg | 348/222.1 |

(Continued)

FOREIGN PATENT DOCUMENTS

WO 2011078869 A1 6/2011

OTHER PUBLICATIONS

Kurz et al., "Close-range hyperspectral imaging for geological field studies: workflow and methods", International Journal of Remose Sensing, vol. 34, No. 5, pp. 1798-1822 (2012).

(Continued)

*Primary Examiner* — Sang Nguyen
(74) *Attorney, Agent, or Firm* — Caesar Rivise, PC

(57) ABSTRACT

A method of investigating a solid sample, in particular a geological sample, such as a borehole core sample, includes the steps of positioning the sample on a sample support device, positioning a hyperspectral camera device, so that a line-shaped surface region of the sample is covered by a field of view of the hyperspectral camera device, illuminating the sample on the sample support device, moving the hyperspectral camera device and the sample support device relative to each other, wherein the field of view of the hyperspectral camera device is moved along a scanning direction over the surface of the sample, and collecting a hyperspectral image of the sample during the moving step, wherein the hyperspectral image is composed of multiple hyperspectral line images.

17 Claims, 3 Drawing Sheets

(56) References Cited

U.S. PATENT DOCUMENTS

| | | | |
|---|---|---|---|
| 2012/0062740 A1* | 3/2012 | Treado et al. | 348/144 |
| 2012/0183213 A1* | 7/2012 | Robles-Kelly et al. | 382/165 |
| 2012/0250017 A1 | 10/2012 | Morys et al. | |
| 2013/0003063 A1* | 1/2013 | Headley et al. | 356/402 |
| 2013/0038725 A1* | 2/2013 | Lanoue et al. | 348/143 |

OTHER PUBLICATIONS

Kurz et al., "Close-range hyperspectral imaging providing new applications in geology", Third annual hyperspectral imaging conference, May 15-16, 2012, Rome, Italy (pp. 1-5, 59-63).

Kurz et al., "Applying hyperspectral imaging for core analysis," CIPR—Petroleum Technology Seminar, Bergen, May 7-8, 2012 (Lecture).

* cited by examiner

METHOD OF INVESTIGATING A SOLID SAMPLE

FIELD OF THE INVENTION

The invention relates to a method of investigating a solid sample using hyperspectral imaging, in particular to a method of investigating solid geological samples, such as borehole core samples. Applications of the invention are available in the fields of analyzing geological samples, like e.g. borehole cores, or other solid materials, like workpieces, paper or food.

TECHNICAL BACKGROUND OF THE INVENTION

It is generally known that extracting cores from oil exploration boreholes is a routine way of sampling and assessing hydrocarbon reservoirs. Borehole cores provide a unique inside into lithology and mineralogy of the subsurface. However, as a general disadvantage of the conventional techniques for investigating borehole cores, the acquisition of data is extremely costly and time consuming. Conventionally, collected cores routinely undergo multiple analyses aimed at describing the mineral composition and petrophysical (rock physics) properties of the rocks. To this end, a series of sub-samples are taken from the core and analyzed with chemical or physical procedures. As a main disadvantage, these sub-sampling procedures and analysis commonly damage or destroy the core material. Furthermore, they provide properties of the core at single positions only, but they do not allow a continuous mapping of the core material or a precise prediction of material properties, like e.g. the material composition or distribution of sample components. Thus, the amount of data that potentially could be retrieved is substantially constrained with the conventional techniques.

Various approaches for spectroscopic investigations of geological samples are known from practice. As an example, the geological sample can be analyzed using a hand-held spectrometer, which provides e.g. reflectivity spectra of a sample's surface at selected measurement positions. Again, this measurement provides information with regard to a few points only, but not a complete image of the sample composition. The amount of spectroscopic data can be increased if the hand-held spectrometer is replaced by an interferometric set-up as described e.g. in WO 2011/078869 A1, U.S. Pat. No. 4,587,424 or US 2012/0250017 A1. However, the use of a scanning interferometer represents a disadvantage in terms of the complexity of the interferometer and the operation thereof as well as with regard to the complex processing of the interferometric spectral data.

Another conventional approach for analyzing geological samples is based on hyperspectral imaging, as described e.g. by T. H. Kurz, S. J. Buckley et al. ("Close-range hyperspectral imaging for geological field studies: workflow and methods" in "International Journal of Remote Sensing" volume 34(5), issue 134, 2013, pp. 1798-1822). The hyperspectral imaging technique is based on the use of absorption characteristics of light to classify the mineralogy of a reflective surface, typically in the near infra-red part of the electromagnetic spectrum. The chemical composition and crystal structure of an object controls how light is reflected and absorbed, giving rise to unique diagnostic features that can be used to identify individual minerals.

With the conventional terrestrial application of hyperspectral imaging, a geological formation, like a cliff section or a surface mining is investigated. A hyperspectral camera having a line-shaped field of view is panned (or: rotated) for collecting a panorama image of the geological formation. Simultaneously, a topological representation is collected with a laser scanner. The hyperspectral image and the topological representation are registered for assigning spectroscopic features to certain surface ranges of geological formation.

Up to now, the hyperspectral imaging is restricted to remote sensing at terrestrial geological formations only. The conventional approach has disadvantages due to a restricted spatial resolution and a limited capability of determining the presence of different materials. Different rock types within a geological formation can be sensed, but an analysis of the rock composition was excluded with the conventional techniques. Furthermore, the practical application of the hyperspectral imaging technique may result in substantial imaging artifacts and problems with regard to image interpretation.

OBJECTIVE OF THE INVENTION

The objective of the invention is to provide an improved method of investigating a solid sample, wherein the method and the device are to be capable of avoiding disadvantages of conventional techniques, resp. In particular, the method is to be conducted with reduced complexity, and it is to be capable to provide hyperspectral images of the sample with improved precision, resolution and/or reproducibility.

BRIEF SUMMARY OF THE INVENTION

According to a general aspect of the invention, the above objective is solved by a method of investigating a solid sample (imaging method), wherein the sample is positioned and illuminated on a sample support device. A hyperspectral camera device is provided such that a line-shaped surface region of the sample is covered by a field of view of the hyperspectral camera device. According to the invention, the hyperspectral camera device and the sample support device are moved relative to each other in order to collect a hyperspectral image of the sample. The movement is conducted such that the line-shaped field of view of the hyperspectral camera device is moved along a scanning direction, e.g. along a longitudinal direction of the sample, over the surface of the sample. During the moving step, multiple hyperspectral line images are taken, which provide the hyperspectral image of the sample to be obtained. Preferably, a homogeneous illumination is provided, including a uniform illumination of each surface region of the sample during the imaging.

For implementing the above imaging method, an imaging device is used, which comprises a sample support device, a hyperspectral camera device, an illumination device, a drive device and a control device including an image processing unit. The sample support device is configured for accommodating the sample to be investigated. The hyperspectral camera device can be adjusted such that a surface region of the sample is covered by a line-shaped field of view of the hyperspectral camera device. The illumination device is arranged for illuminating the sample support device. The drive device is adapted for moving the hyperspectral camera device and the sample support device relative to each other. Thus, the field of view of the hyperspectral camera device can be moved along a scanning direction over the surface of the sample support device carrying the sample. Finally, the image processing unit is configured for providing a hyperspectral image of the sample on the basis of multiple hyperspectral line images collected with the hyperspectral camera device.

The hyperspectral camera device generally is an optical camera device including at least one spectrally dispersive element, such as spectrally dispersive refractive or reflective element(s) and/or at least one tunable optical bandpass filter, and a two-dimensional detector, such as a CCD-detector. The hyperspectral camera device has a line-shaped field of view, wherein a line-shaped region of the sample surface is imaged with camera optics along the first dimension of the two-dimensional detector, while a spectrum is collected for each pixel of the line-shaped portion along the second dimension of the two-dimensional detector. The spectrum covers a spectral range determined by the features of the at least one spectrally dispersive element and/or the at least one tunable optical bandpass filter. Preferably, the hyperspectral camera device is arranged such that the line-shaped field of view thereof is extending perpendicular to the scanning direction, i.e. perpendicular to the direction of the mutual movement of the sample support device and the hyperspectral camera device. Furthermore, preferably, the surface of the sample and the scanning direction have a horizontal orientation.

As a main advantage of the invention, the mutual movement of the sample support device and the hyperspectral camera device in combination with the illumination of the sample on the sample support device allows a rapid, reasonably inexpensive, extremely accurate and non-destructive high-resolution imaging of the sample, in particular a borehole core sample. The sample support device allows a precise and reproducible positioning of the sample relative to the hyperspectral camera device. Imaging artifacts can be minimized, and the spatial resolution can be essentially improved compared with the conventional techniques. Furthermore, the precise mutual adjustment of the sample and the hyperspectral camera device facilitates a quantitative evaluation of the images collected. According to an advantageous embodiment of the invention, the collection of an additional topological image of the sample can be provided, e.g. using a laser profiler. The additional topological image may have advantages in terms of automatically identifying missing parts of the sample, e.g. natural vugs or fractures in a geological sample.

A spatial resolution of hyperspectral imaging can be obtained, which has not been reached so far, e.g. with a surface size of 1 mm per pixel of the hyperspectral camera device. The increased precision of hyperspectral imaging allows a quantification of the sample composition. As an example, the percentage of certain sample materials can be calculated.

Furthermore, the mutual movement of the sample support device and the hyperspectral camera device allows a continuity of sampling. For the first time, a real image-based technique is provided for hyperspectral imaging solid samples. With the invention, a high resolution mapping of materials and geological features e.g. in a borehole core can be obtained. This allows the investigation of potential correlations with petrophysical properties through investigating material differences within the sample. Furthermore, the inventive method is fast and efficient, and it can be conducted in a non-destructive manner.

As a further advantage, the combined use of the sample support device and the hyperspectral camera device allows for the provision of a portable apparatus. The complete imaging device can be transported to an application site by the user, and the inventive method can be practically implemented at a location of collecting the samples, e.g. directly at a borehole core store. This represents an essential advantage as a transport of the mechanically sensitive borehole core materials can be avoided.

According to a preferred embodiment of the invention, the sample is illuminated with at least one electrical light source being directed on the field of view of the hyperspectral camera. Contrary to the conventional terrestrial applications, the sunlight illumination is replaced by the illumination with the at least one electrical light source. Advantageously, the illumination conditions are provided with essentially increased precision and stability. Imaging artifacts resulting from changing sunlight illuminations in the conventional techniques are avoided. The at least one electrical light source can be controlled such that the illumination conditions, in particular the intensity and the spectral composition of the illumination light, are constant during the measurement of the sample or during multiple measurements of different samples.

According to a particularly preferred embodiment of the invention, the at least one electrical light source and the hyperspectral camera device have a fixed position relative to each other. Accordingly, the illumination conditions are further stabilized during collecting the hyperspectral line images.

Advantageously, the particular type of the at least one electrical light source used with the invention can be selected in dependency on the spectral properties of the sample and/or the spectral sensitivity of the hyperspectral camera device. In particular, the at least one electrical light source is adapted for emitting at least one wavelength in the ultraviolet, visible and/or infrared wavelength range. Preferably, the at least one electrical light source comprises a broad band light source, like e.g. a halogen lamp or a discharge lamp.

With a further preferred embodiment of the invention, two electrical light sources are operated, which illuminate the sample from two different directions. With a preferred example, the electrical light sources are arranged on different sides of the hyperspectral camera device relative to the viewing direction thereof. Thus, the sample is illuminated from opposite directions relative to the viewing direction. Illumination fields of both electrical light sources are superimposed on the sample surface. As a main advantage, this provides a full illumination of the sample surface, while micro-shadowing due to surface structures is avoided. In particular, the provision of two electrical light sources improves the homogeneity of illumination.

If the electrical light sources have equal illumination fields, and if they illuminate the sample with equal but opposite angles of incidence, a line-shaped illumination area is provided which advantageously is adapted to the line-shaped field of view of the hyperspectral camera device. Thus, maximum homogeneous illumination can be obtained in the field of view.

For the homogeneous illumination of the sample on the sample support device, the at least one electrical light source preferably is arranged adjacent to the hyperspectral camera device. According to an advantageous embodiment of the invention, a shielding device can be arranged between the illumination device and the hyperspectral camera device in order to shield scattering light being directed from the at least one electrical light source to the hyperspectral camera device.

Advantageously, multiple variants of implementing the mutual movement of the sample support device and the hyperspectral camera device are available. According to a first variant, the mutual movement comprises a linear translation. With this embodiment, it is preferred that the sample support device is translated along the scanning direction relative to the fixed hyperspectral camera device. Accordingly, the scanning direction is opposite to the translation direction of the sample support device. Alternatively, the hyperspectral camera device can be translated along the scanning direction relative to a fixed sample support device. According to yet another alternative variant, the mutual movement comprises a pivoting or panning movement of the hyperspectral camera device relative to the sample support device.

With the preferred embodiment of moving the sample support device relative to the hyperspectral camera device, the sample support device is connected with a drive device, which is configured for translating the carrier platform parallel to the scanning direction. With preferred examples, the sample support device comprises a moveable table, which can be translated with the drive device, or an endless belt conveyor providing the carrier platform and being operated with the drive device. Preferably, the drive device is adapted for a step-wise movement of the sample support device.

According to a further preferred embodiment of the invention, a synchronization of the operation of the hyperspectral camera device with the mutual movement of the hyperspectral camera device and the sample support device is provided. Advantageously, this allows a homogeneous imaging of the sample surface along the scanning direction.

According to a further preferred embodiment of the invention, the hyperspectral camera device is connected to a rack. The rack has a fixed position in a laboratory system. Accordingly, the hyperspectral camera device has a fixed position, while the inventive moving step is conducted by moving the sample support device relative to the rack. Preferably, the rack comprises a dismountable rack module structure. Advantageously, the imaging device has a compact structure. Accordingly, the distance between the hyperspectral camera device and the sample support device preferably is below 2 m, in particular below 1.5 m.

According to a further advantageous embodiment of the invention, the hyperspectral images are calibrated using calibration material, which is arranged beside the sample or image with a separate image calibration step. The calibration material includes at least one diffuse reference reflector, which preferably is arranged on the sample support device, and/or at least one calibration image.

Typically, the hyperspectral camera device itself is calibrated by the manufacturer, so that an additional camera calibration is possible but not necessary. By collecting at least one hyperspectral image with the at least one diffuse reference reflector having known spectral properties, the collected data can be calibrated. The reflectivity of the diffuse reference reflector can be selected in dependency on the measuring conditions, in particular in the range from 2% to 99%. Furthermore, multiple diffuse reference reflectors, preferably two reflectors, can be used for calibrating the hyperspectral images.

As a further advantage of the invention, the collected hyperspectral image allows for a further step of creating a quantitative image map of sample material included in the sample. As an example, the image map comprises a map of minerals included in a rock sample. With a preferred modification, the quantitative image map additionally may include sample material concentrations. In this case, the image map does not only provide the distribution of the sample materials, like e.g. minerals, but also the concentrations thereof. Furthermore, a distribution of the sample materials can be visualized, in particular with a false color diagram, e.g. using a display device or a printer. With this embodiment, the inventive method offers a way to guide an image interpretation for the user, e.g. by highlighting material changes. In particular, this can be included in the visualization without the user having to additionally examine each sample, e.g. borehole core, in detail physically or using conventional imaging.

Advantageously, the invention can be used for investigating various types of samples. According to preferred applications of the invention, the sample comprises a geological sample, in particular a rock sample, such as a borehole core sample, which may be e.g. a consolidated or unconsolidated sediment sample, a metamorphic rock sample, an igneous rock sample, a sandstone sample, a claystone sample and/or a breccia sample. The sample may include a solid sample or a powder sample. The sample includes multiple sample materials, like e.g. multiple minerals or organic components in a geological sample. With alternative applications, the invention can be applied e.g. in paper industry for investigating paper samples or in food industry for investigating food samples.

The sample support device used according to the invention, generally comprises a carrier with a carrier platform accommodating the sample. Preferably, the carrier platform has a horizontal orientation, i.e. the sample accommodated by the sample support device has a surface extending in a horizontal direction. However, depending on the application of the invention, other orientations of the carrier platform of the sample support device and the sample's surface are possible.

BRIEF DESCRIPTION OF THE DRAWINGS

Further details and advantages of the invention are described in the following with reference to the attached drawings, which show in.

PREFERRED EMBODIMENTS OF THE INVENTION

Preferred embodiments of the invention are described in the following with particular reference to the arrangement of the hyperspectral camera device and the sample support device, the implementation of the relative movement thereof, the illumination of the sample and the collection of hyperspectral images. Details of the hyperspectral camera device are not described as far as they are known from commercially available hyperspectral cameras. Furthermore, details of the processing of the hyperspectral images and the evaluation of spectral properties of a sample are not described as far as they are known from conventional applications of hyperspectral cameras.

In the following, reference is made in an exemplary manner to an application of the invention, wherein borehole core samples are investigated. It is emphasized that the implementation of the invention is not restricted to this type of samples, but rather possible with other types of solid samples, in particular other geological rock samples or other work pieces or materials, like e.g. paper or food.

Figure 1:
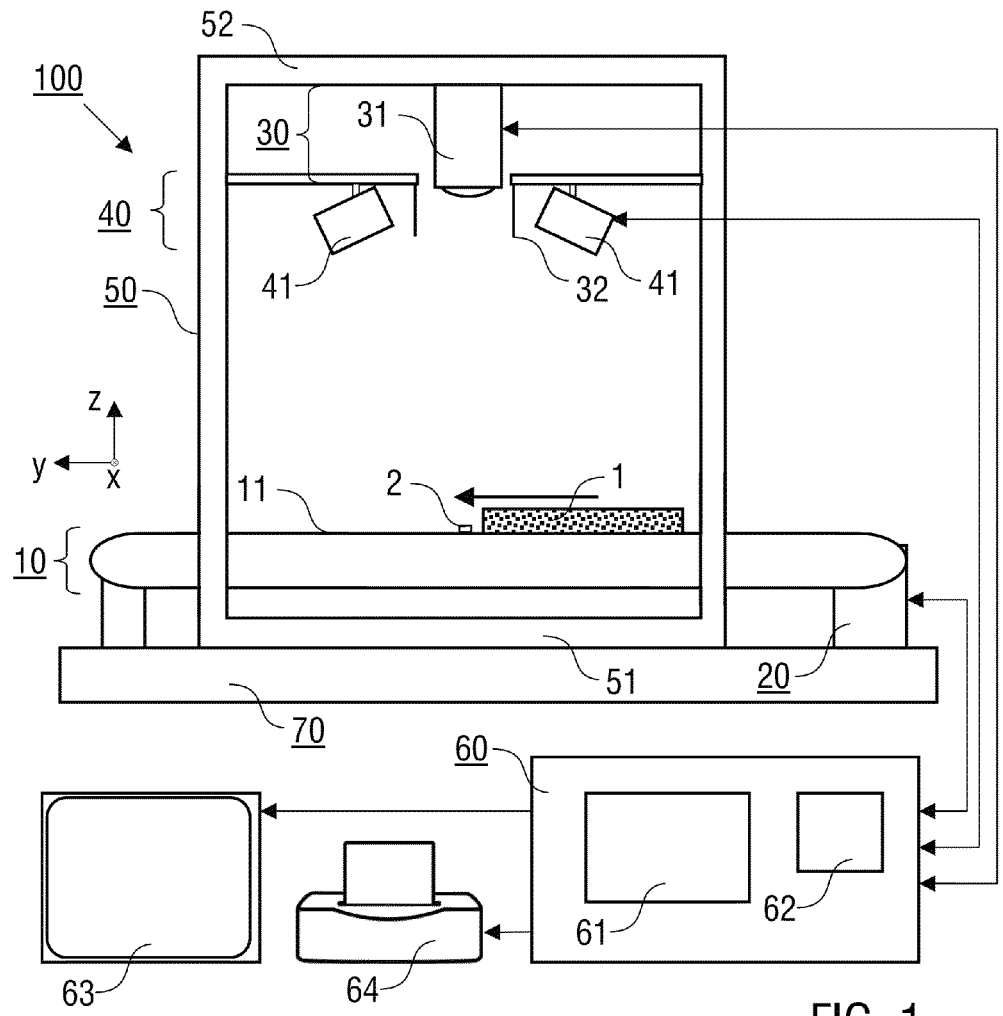
FIG. 1: a schematic illustration of an imaging device used according to a first embodiment of the inventive imaging method.

FIG. 1 schematically shows a first example of an imaging device 100 used according to a first embodiment of the invention. The imaging device 100 comprises a sample support device 10, a drive device 20, a hyperspectral camera device 30, an illumination device 40, a rack 50 and a control device 60 including an image processing unit 61. The imaging device 100 is positioned e.g. in a laboratory room, in particular on the bottom or a stable table 70 thereof. The above components are described in the following with reference to a Cartesian coordinate system, wherein the x- and y-directions span a horizontal plane, while the z-direction is vertically oriented.

The sample support device 10 used for implementing the inventive method preferably comprises a carrier platform (carrier table), which is supported by guide rails via support wheels and which can be step-wise translated along the guide rails with a drive device or, according to an alternative as shown in FIG. 1, a step-moveable conveyor belt 11, the upper surface of which providing a carrier platform accommodating the sample 1. The sample 1 is a borehole core having a longitudinal length (y-direction) of e.g. 1 m and a width (x-direction) of e.g. 15 cm. The conveyor belt 11 is driven with the drive device 20, including e.g. an electric motor, which is controlled with the control device 60. When the conveyor belt 11 is moved step-wise relative to the fixed hyperspectral camera device 30, the sample 1 is linearly translated parallel to the longitudinal extension of the conveyor belt 11 (y-direction). With a practical example, the carrier platform of the conveyor belt 11 has a length in y-direction of about 1.02 m and a width in x-direction of about 0.30 m.

The hyperspectral camera device 30 comprises a hyperspectral camera 31, like e.g. the commercial camera HySpex SWIR-320 m, which is mounted to the rack 50. The rack 50 preferably has a box shape as shown. Bottom beams 51 of the rack 50 are placed on the bottom 70 of the laboratory. The bottom beams 51 provide a space accommodating the sample support device 10. The hyperspectral camera 31 is mounted to the upper beams 52 of the rack 22, or alternatively the camera is mounted to one of the vertical beams, e.g. at the rear of the rack. The camera is not fixed, but an adjustment is provided to ensure a correct distance between the camera 31 and the sample 1. This distance can vary depending on the sample thickness. During image acquisition, the vertical distance is constant, as the camera has a fixed adjustment position. With an example (not shown), the hyperspectral camera 31 is fixed to a vertical beam at the backside of the rack 22 and is adjustable in z-direction.

The hyperspectral camera 31 is adjusted such that a line-shaped field of view 2 thereof is focused on the upper surface of the sample support device 10, in particular on the upper surface of the conveyor belt 11. Due to a depth of field covering the sample thickness in z-direction, the hyperspectral camera 31 is focused onto the sample 1 as well. The line-shaped field of view 2 is oriented along the x-direction, i.e. perpendicular to the longitudinal extension of the conveyor belt 11, and the optical path from the hyperspectral camera 31 to the sample support device 10 is vertically oriented. While the hyperspectral camera 31 has a fixed position, e.g. in the center between the upper beams 52 of the rack 50, it can be adjustable in the vertical direction, e.g. for focusing purposes. The hyperspectral camera 31 is connected with the control device 60 for collecting multiple hyperspectral line images during the translation of the sample 1 by the conveyor belt 11. As an example, the camera HySpex SWIR-320 m records images in the infrared wavelength range with 320 pixels covering the camera's field of view.

The illumination device 40 comprises two light sources 41, like e.g. halogen lamp tubes, which are mounted at the rack via vertical beams at the backside of the rack. Alternatively, the lamps can be separately arranged using tripods, or they can be fixed to the hyperspectral camera 31 (see FIG. 3). The light sources 41 are directed towards the line-shaped field of view 2 of the hyperspectral camera 31. The field of view 2 is illuminated from two different sides relative to the camera's viewing direction, so that a line-shaped homogeneous illumination is obtained. The light sources 41 are arranged adjacent to the objective of the hyperspectral camera 31. In order to shield scattering light, a shielding device 32, e.g. with the shape of a hollow cylinder, is arranged between the light sources 41 and the objective of the hyperspectral camera 31.

Figure 2:
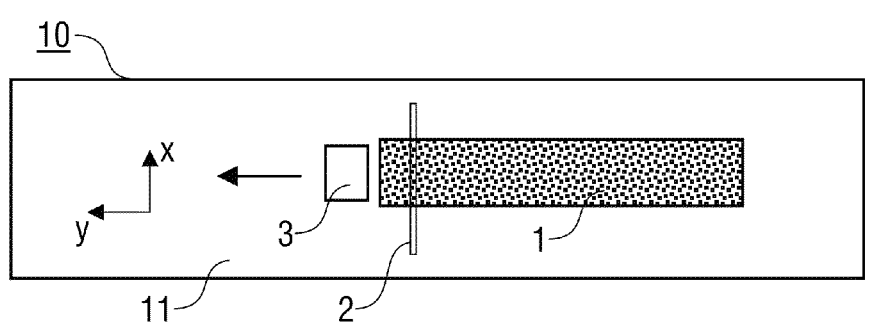
FIG. 2: a schematic plan view on a sample support device used according to the invention.

FIG. 2 schematically illustrates a plan view on the sample support device 10. The upper surface of the conveyor belt 11 provides the carrier platform, onto which the line-shaped field of view 2 of the hyperspectral camera 31 (see FIG. 1) is focused. The sample 1 is arranged on the upper surface of the sample support device 10. Furthermore, at least one reference reflector 3 is positioned adjacent to the sample 1 for calibrating purposes. By operating the drive device 20 (see FIG. 1), the sample 1 is moved in y-direction, so that the field of view 2 is scanned in a scanning direction over the surface of the sample 1. The scanning direction is opposed to the translation direction of the sample 1.

FIG. 1 further illustrates the control device 60, which includes the image processing unit 61 and a synchronization unit 62. With the synchronization unit 62, the operation of the hyperspectral camera 31 and the drive device 20 is synchronized. As an example, the synchronization unit 62 includes a translation stage controller connected with the drive device 20. When the collection of one single hyperspectral line image of a sample surface section is confirmed by the hyperspectral camera 31, the translation stage controller activates the drive device 20 for moving an adjacent sample surface section into the field of view 2 of the hyperspectral camera 31. Accordingly, multiple hyperspectral line images can be collected in step-wise fashion and precisely assigned to a series of adjacent surface sections of the sample 1.

With the image processing unit 61, the hyperspectral line images are processed for providing the complete hyperspectral image of the sample 1. The control device 60 can be implemented using a computer circuit or a microcontroller connected with a calculation processor. Furthermore, the control device 60 is connected with components for a visualization of the hyperspectral image or a qualitative image map, like e.g. a display 63 and/or a printer 64.

The example of the imaging device 100 as shown in FIG. 1 can be modified as follows. The box-shaped rack 50 can be replaced by a tripod-shaped rack, e.g. a pillar tripod holding the camera above the sample support device, or a rack having another structure. Furthermore, the illumination device 40 can be fixed directly to the rack 50. Furthermore, a continuous operation can be implemented instead of the step-wise movement and collection of hyperspectral line images.

Figure 3:
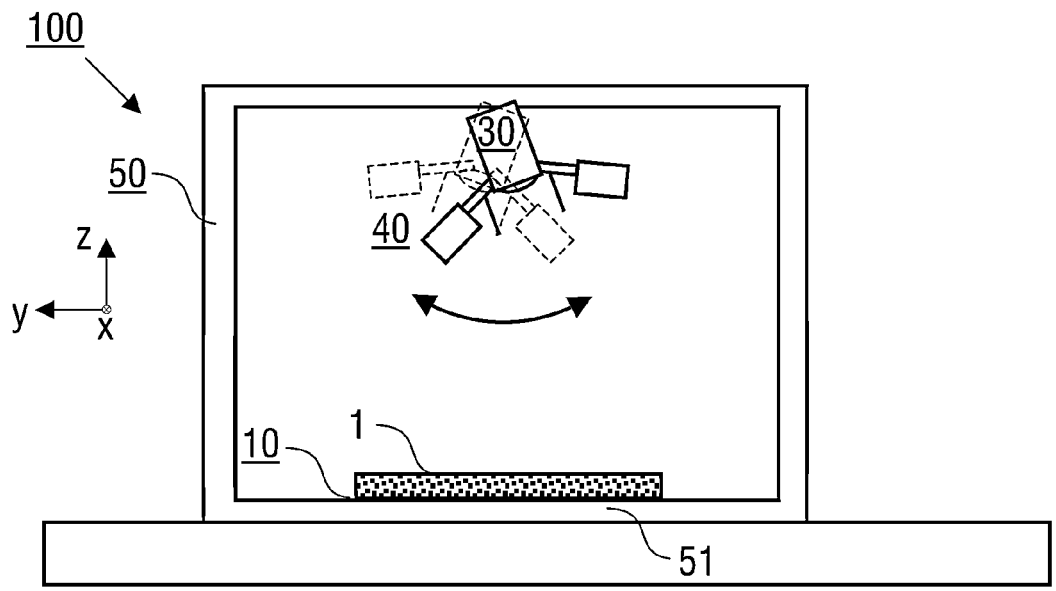
FIG. 3: a schematic illustration of a modified imaging device used according to a further embodiment of the inventive imaging method.

Furthermore, the hyperspectral camera device 30 and the illumination device 40 can be arranged in a moveable manner at the upper beams 52 of the rack 50. As shown in FIG. 3, the imaging device 100 of this example comprises a fixed sample support device 10 accommodating the sample 1. The sample support device 10 is provided as a fixed platform on the bottom beams 51 of the rack 50. The sample support device 10 and the sample 1 have a fixed position in space, while the hyperspectral camera device 30 and the illumination device 40 are step-wise panned with a drive device (not shown) relative to the sample 1 (see arrow). Accordingly, the field of view of the hyperspectral camera device 30 is moved over the surface of the sample 1 along the fixed scanning direction (positive or negative y-direction). Further details of the imaging device, in particular the control device thereof, are provided as described with reference to FIG. 1.

Figure 4:
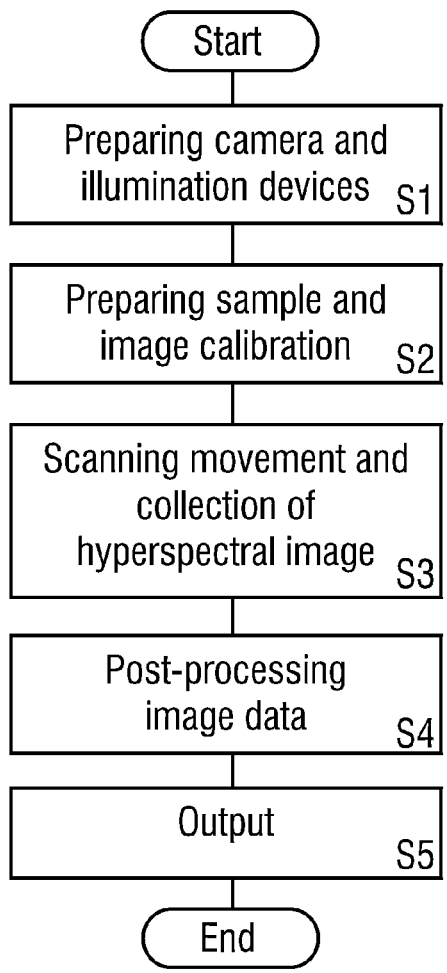
FIG. 4: a flow-chart illustrating an embodiment of the inventive imaging method.

FIG. 4 illustrates the main steps of conducting a method of investigating the sample 1 according to a preferred embodiment of the invention. With a first step S1, the hyperspectral camera and illumination devices 30, 40 are prepared. The hyperspectral camera 31 is adjusted for a vertical illumination of the sample 1 on the sample support device 10 (see FIG. 1).

The width of the line-shaped field of view is adjusted in dependency on the spatial resolution of the hyperspectral imaging to be obtained. Furthermore, the light sources 41 are adjusted for a homogeneous illumination of the field of view. With step S2, the sample is prepared. As an example, the borehole core is positioned as the sample 1 on the sample support device 10 so that the longitudinal core direction is in parallel with the translation direction of the sample support device 10 (y-direction). The sample 1 is provided with a clean surface, but without a polishing or an additional coating. Calibration material is positioned next to the sample (see FIG. 2). Alternatively, when it can be assumed that the illumination is constant between separate images, the calibration material is scanned with a separate image to acquire data for image calibration.

Subsequently, the drive device 20 is operated so that the sample 1 is step-wise translated through the field of view of the hyperspectral camera 31. During this scanning movement multiple hyperspectral line images are taken with the hyperspectral camera 31. The scanning movement steps and the collection of the hyperspectral line images are conducted in an alternating manner. At least one hyperspectral line image is taken per step. Preferably, the number of hyperspectral line images is equal to the number of scanning steps. As an example, with 2000 scanning steps per meter, 2000 hyperspectral line images are taken. The hyperspectral line images are processed for creating the complete hyperspectral image using the image processing unit 61. Subsequently, a post-processing of image data is conducted with step S4. As an example, a quantitative map of the sample surface is created by comparing the collected spectral properties of the sample surface with predetermined reference spectra of minerals included in the sample. Finally with step S5, the quantitative image map is presented to the user, e.g. displayed on the display 63 or printed with the printer 64.

Figure 5:
FIGS. 5 and 6: exemplary illustrations of practical results obtained with the invention.
Figure 6:
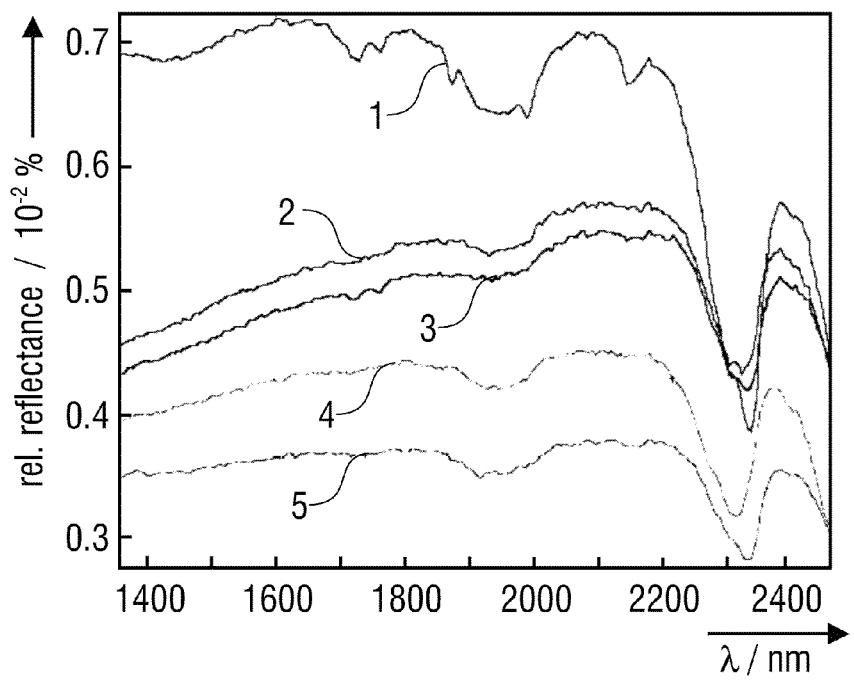

Practical results of hyperspectral imaging a sand stone borehole core are illustrated in FIGS. 5 and 6. FIG. 5 shows a quantitative image map of a carbonate based borehole core, wherein different grey values represent different minerals included in the sample 1, such as a calcite matrix, dolomite regions, clay regions etc. The quantitative image map is generated on the basis of the different spectroscopic properties of the sample materials included in the sample. FIG. 6 shows different spectra in the infrared wavelength range, which represent in an exemplary manner different sample materials, such as bio-particles (curve 1), matrix with medium dolomite concentration (curve 2), calcite matrix (curve 3), dolomite matrix (curve 4) and clay sections (curve 5). By analyzing the different spectra in the hyperspectral image, the sample materials can be mapped and visualized for the user.

The features of the invention disclosed in the above description, the drawings and the claims can be of significance both individually as well as in combination for the realization of the invention in its various embodiments.

What is claimed is:

1. A method of investigating a solid sample, comprising the steps of:
    positioning the sample on a sample support device,
    positioning a hyperspectral camera device, so that a line-shaped surface region of the sample is covered by a field of view of the hyperspectral camera device,
    illuminating the sample on the sample support device,
    moving the hyperspectral camera device and the sample support device relative to each other, wherein the field of view of the hyperspectral camera device is moved along a scanning direction over the surface of the sample and the moving step comprises step-wise mutual movement of the hyperspectral camera device and the sample support device relative to each other, and
    collecting a hyperspectral image of the sample during the moving step, wherein the hyperspectral image is comprised of multiple hyperspectral line images, and wherein the collecting of the hyperspectral line images with the hyperspectral camera device is synchronized with the step-wise mutual movement of the hyperspectral camera device and the sample support device, so that the hyperspectral line images homogeneously cover the surface of the sample along the scanning direction.

2. The method according to claim 1, wherein the illuminating step comprises illuminating the sample with at least one electrical light source being directed on the field of view of the hyperspectral camera device.

3. The method according to claim 2, wherein the at least one electrical light source and the hyperspectral camera device have a fixed position relative to each other.

4. The method according to claim 2, wherein the at least one electrical light source is adapted for emitting at least one of ultraviolet, visible and infrared light.

5. The method according to claim 2, wherein the illuminating step comprises illuminating the sample with two electrical light sources being directed from different sides relative to the viewing direction of the hyperspectral camera device onto the field of view of the hyperspectral camera device.

6. The method according to claim 1, wherein the field of view of the hyperspectral camera device has a line shape extending perpendicular to the scanning direction.

7. The method according to claim 1, wherein the moving step includes translating the hyperspectral camera device and the sample support device relative to each other parallel to the scanning direction.

8. The method according to claim 7, wherein the moving step includes translating the sample support device parallel to the scanning direction relative to the hyperspectral camera device at a fixed position.

9. The method according to claim 1, wherein the moving step includes pivoting the hyperspectral camera device relative to the sample support device.

10. The method according to claim 1, wherein the surface of the sample and the scanning direction have a horizontal orientation.

11. The method according to claim 1, wherein
    the hyperspectral camera device is connected to a rack with a fixed position in a laboratory system, and
    the moving step comprises moving the sample support device relative to the rack.

12. The method according to claim 1, further comprising calibrating the hyperspectral images using at least one of at least one diffuse reference reflector, at least one position marker and at least one calibration image.

13. The method according to claim 1, further comprising creating a quantitative image map of sample materials included in the sample.

14. The method according to claim 13, further comprising creating a quantitative image map of sample material concentrations included in the sample.

15. The method according to claim 1, further comprising presenting a visualization of a distribution of the sample materials.

16. The method according to claim 1, wherein the sample comprises at least one of a borehole core sample, a rock sample, a consolidated or unconsolidated sediment sample, a metamorphic rock sample, an igneous rock sample, a sandstone sample, a claystone sample, a breccia sample, a powder sample, a paper material sample, and a food sample.

17. A method of investigating a solid sample, comprising the steps of:
   positioning the sample on a sample support device,
   positioning a hyperspectral camera device, so that a line-shaped surface region of the sample is covered by a field of view of the hyperspectral camera device,
   illuminating the sample on the sample support device,
   moving the hyperspectral camera device and the sample support device relative to each other, wherein the field of view of the hyperspectral camera device is moved along a scanning direction over the surface of the sample,
   collecting a hyperspectral image of the sample during the moving step, wherein the hyperspectral image is comprised of multiple hyperspectral line images, and
   calibrating the hyperspectral line images using at least one of at least one diffuse reference reflector, at least one position marker and at least one calibration image.

* * * * *